United States Patent
Hossainy

(10) Patent No.: US 7,438,722 B1
(45) Date of Patent: *Oct. 21, 2008

(54) METHOD FOR TREATMENT OF RESTENOSIS

(75) Inventor: Syed F. A. Hossainy, Fremont, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/251,097

(22) Filed: Sep. 20, 2002

(51) Int. Cl.
A61F 2/06 (2006.01)
A61K 9/22 (2006.01)

(52) U.S. Cl. .................. 623/1.42; 623/1.46; 604/890.1; 600/36

(58) Field of Classification Search ................. 424/426; 604/890.1; 623/1.42–1.44
See application file for complete search history.

(56) References Cited

U.S. PATENT DOCUMENTS

| | | | | |
|---|---|---|---|---|
| 4,977,901 A | 12/1990 | Ofstead | | 128/772 |
| 5,061,738 A * | 10/1991 | Solomon et al. | | 523/100 |
| 5,112,457 A | 5/1992 | Marchant | | 204/165 |
| 5,171,217 A * | 12/1992 | March et al. | | 604/507 |
| 5,318,780 A * | 6/1994 | Viegas et al. | | 424/427 |
| 5,328,471 A | 7/1994 | Slepian | | 604/101 |
| 5,399,351 A * | 3/1995 | Leshchiner et al. | | 424/422 |
| 5,455,040 A | 10/1995 | Marchant | | 424/426 |
| 5,464,650 A | 11/1995 | Berg et al. | | 427/2.3 |
| 5,575,815 A * | 11/1996 | Slepian et al. | | 600/36 |
| 5,578,073 A | 11/1996 | Haimovich et al. | | 623/1 |
| 5,605,696 A | 2/1997 | Eury et al. | | 424/423 |
| 5,667,767 A | 9/1997 | Greff et al. | | 424/9.411 |
| 5,670,558 A | 9/1997 | Onishi et al. | | 523/112 |
| 5,700,286 A | 12/1997 | Tartaglia et al. | | 623/1 |
| 5,716,981 A | 2/1998 | Hunter et al. | | 514/449 |
| 5,824,049 A | 10/1998 | Ragheb et al. | | 623/1 |
| 5,830,178 A | 11/1998 | Jones et al. | | 604/49 |
| 5,837,313 A | 11/1998 | Ding et al. | | 427/2.21 |
| 5,851,508 A | 12/1998 | Greff et al. | | 424/9.411 |
| 5,858,746 A | 1/1999 | Hubbell et al. | | 435/177 |
| 5,865,814 A | 2/1999 | Tuch | | 604/265 |
| 5,873,904 A | 2/1999 | Ragheb et al. | | 623/1 |
| 5,893,839 A * | 4/1999 | Johnson | | 604/506 |
| 5,971,954 A | 10/1999 | Conway et al. | | 604/96 |
| 5,980,928 A | 11/1999 | Terry | | 424/427 |
| 5,980,972 A | 11/1999 | Ding | | 427/2.24 |
| 6,015,541 A | 1/2000 | Greff et al. | | 424/1.25 |
| 6,042,875 A | 3/2000 | Ding et al. | | 427/2.24 |
| 6,051,607 A | 4/2000 | Greff | | |
| 6,051,648 A | 4/2000 | Rhee et al. | | 525/54.1 |
| 6,056,993 A | 5/2000 | Leidner et al. | | 427/2.25 |
| 6,060,451 A | 5/2000 | DiMaio et al. | | 514/13 |
| 6,080,488 A | 6/2000 | Hostettler et al. | | 428/423.3 |
| 6,096,070 A | 8/2000 | Ragheb et al. | | 623/1 |
| 6,099,562 A | 8/2000 | Ding et al. | | 623/1.46 |
| 6,110,188 A | 8/2000 | Narciso, Jr. | | 606/153 |
| 6,113,629 A | 9/2000 | Ken | | 623/1.1 |
| 6,120,536 A | 9/2000 | Ding et al. | | 623/1.43 |
| 6,120,904 A | 9/2000 | Hostettler et al. | | 428/423.3 |
| 6,121,027 A | 9/2000 | Clapper et al. | | 435/180 |
| 6,129,761 A | 10/2000 | Hubbell | | 623/11 |
| 6,153,252 A | 11/2000 | Hossainy et al. | | 427/2.3 |
| 6,160,032 A | 12/2000 | Shah et al. | | |
| 6,165,212 A | 12/2000 | Dereume et al. | | 623/1.13 |
| 6,565,601 B2 * | 5/2003 | Wallace et al. | | 623/1.15 |
| 6,585,765 B1 | 7/2003 | Hossainy et al. | | |
| 6,610,035 B2 * | 8/2003 | Yang et al. | | 604/265 |
| 6,749,626 B1 * | 6/2004 | Bhat et al. | | 623/1.1 |
| 2001/0053356 A1 * | 12/2001 | Mousa | | 424/94.1 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

OTHER PUBLICATIONS

Slepian, M. et al "Polymeric endoluminal gel paving" Adv. Drug Del. Rev. (1997) vol. 24, pp. 11-30.*

Udipi, K. et al "Modification inflammatory response . . . " J. Biomed. Mater. Res.(2000) vol. 51, No. 4, pp. 549-560.*

Gutaowska, A. et al "Injectable gels for tissue engineering" The Anatomical Record (2001) vol. 263, pp. 342-349.*

Hakert, H. et al "Rheological and electron microscopic characterization of aqueous carboxymethylcellulose gels . . . " Colloid Polym. Sci. (1989) vol. 267, pp. 226-229.*

Fram, D. et al "Local delivery of heparin to balloon angioplasty sites . . . " Cath. Cardiovasc. Diag. (1997) vol. 41, pp. 275-286.*

Safety data sheet for Pluronic(tm) L44. Accessed online Apr. 15, 2007.*

Okada, T. et al "Local anticoagulation without systemic effect . . . " Stroke (1988) vol. 19, No. 12, pp. 1471-1476.*

Kiesz, R. et al "Local delivery of enoxaparin to decrease restenosis after stenting . . . " Circulation (2001) vol. 103, pp. 26-31.*

* cited by examiner

Primary Examiner—Leigh C Maier
(74) Attorney, Agent, or Firm—Squire, Sanders & Dempsey L.L.P.

(57) ABSTRACT

A method for inhibiting restenosis is described. The method comprises implanting a stent in a patient's vasculature and simultaneously delivering a restenosis-inhibiting medicine to the treatment site by adjuvant therapy.

38 Claims, No Drawings

METHOD FOR TREATMENT OF RESTENOSIS

BACKGROUND

1. Field of the Invention

This invention relates to the prevention, reducing the formation or treatment of restenosis.

2. Description of the Sate of the Art

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the vessel wall. The balloon is then deflated to a smaller profile to allow the catheter to be withdrawn from the patient's vasculature.

A problem associated with the procedure includes formation of intimal flaps or torn arterial linings that can collapse and occlude the conduit after the balloon is deflated. Moreover, thrombosis and restenosis of the artery can develop over several months after the procedure, which can require another angioplasty procedure or a surgical bypass operation. To reduce the partial or total occlusion of the artery by the collapse of arterial lining and to reduce the chance of the development of thrombosis and restenosis, a stent is implanted in the lumen to maintain the vascular patency. Stents are scaffolding structures, usually cylindrical or tubular in shape, functioning to physically hold open, and if desired, to expand the wall of the passageway. Typically stents are capable of being compressed for insertion through small lumens via small catheters, and then expanded to a larger diameter once at the desired location.

To treat the damaged vasculature tissue and further fight against thrombosis and restenosis, there is also a need to administer therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular cells, respectively. To provide an efficacious concentration to the treated site, systemic administration of the medication can produce adverse or toxic side effects for the patient. Local delivery is a highly suitable method of treatment in that smaller levels of medication, as compared to systemic dosages, are concentrated at a specific site. Local delivery produces fewer side effects and achieves more effective results.

In addition to providing mechanical functionality, stents are being modified to provide biological therapy. One method of medicating stents involves the use of a polymeric carrier coated onto the body of the stent. A polymer dissolved in a solvent, and a therapeutic substance added thereto, is applied to stent and the solvent is removed to form the coating. Subsequent to the implantation of the stent, the medication is released from the polymeric coating. Although drug eluting vascular stents have illustrated significant results for the treatment of restenosis, there is a need for improved methods of the treatment of this condition.

SUMMARY

A method for inhibiting restenosis is provided, the method comprises implanting a stent in a patient's vasculature, wherein the stent is coated with a polymeric layer containing a first substance; and contemporaneously with the act of implanting the stent, delivering a second substance to the treatment site by a means of adjuvant delivery. In one embodiment, the second substance does not precipitate when the substance comes into contact with blood and has a viscosity of not less than 5 centipoise. In yet another embodiment, the second substance includes an amount of water so as to prevent the second substance from precipitating when the composition is exposed to blood.

The first substance or the second substance can include poly(ethylene glycol), PLURONIC polyols, palmitates, stearates, tridodecylmethylammonium chloride, a TWEEN surfactant, sodium dodecyl sulfate, heparin stearate, heparin palmitate, surfactant protein from alveolar fluid, surfactant protein A, surfactant protein D, and lung surfactant S-TA.

In yet another embodiment, the first or second substance can include estradiol, paclitaxel, heparin, heparin derivatives containing hydrophobic counter-ions, docetaxel, rapamycin, structural derivatives of rapamycin, and functional analogs of rapamycin.

In yet another embodiment, the first or second substance can include sodium chloride or potassium chloride.

In yet another embodiment, the first or second substance can include garlic oil, castor oil, hyaluronic acid, carboxymethyl cellulose, ethanol, xylene, and superoxide mimetics, and combinations thereof.

In yet another embodiment, the first or second substance can be a low molecular weight salt.

DETAILED DESCRIPTION

According to embodiments of the present invention, a coated stent is provided. The coating can include a drug-polymer layer for the sustained release of a drug or therapeutic substance; an optional primer layer serving as an adhesive tie layer between the drug-polymer layer and the surface of the stent; an optional topcoat layer for reducing the rate of release of the therapeutic substance; and an optional finishing layer for providing better biocompatibility for the coating. The topcoat layer and/or the finishing layer can also contain a medicine.

The medicine incorporated into the stent can include a surfactant, a low molecular weight salt, a drug, or other compounds having beneficial therapeutic or prophylactic properties. A non-medicated stent can be used with the practice of the present invention; however, a medicated stent is preferred. Body fluids will penetrate the coating and the surfactant can gradually dissolve in the body fluids and can be carried to the diseased site. As a result, the surfactant can denature the cells into which it is incorporated, thus reducing inflammatory cell activation. This can lead to the inhibition of the vascular smooth muscle cell migration and/or proliferation, for the treatment of restenosis. The salts, if used, can also penetrate the cells of the tissue at the diseased site and destroy the restenosis cells by altering local environmental toxicity. If a combination of the drug and the surfactant is used as the medicine, the surfactant can also serve as a permeation enhancer. Consequently, there is a possibility that an additional synergistic therapeutic effect can be achieved. Particular kinds of surfactants, low molecular weight salts, drugs, or other compounds having beneficial therapeutic or prophylactic effect that can be used are discussed below.

In order to achieve better restenosis inhibition, additional compounds are administered via peri-procedural adjuvant therapy procedure. "Inhibition" is defined as reduction, elimination, prevention, or treatment of the condition and includes delaying the onset of the cellular activity leading to the condition. The term "peri-procedural delivery" is defined as delivery at about the same time as the time of deployment or implantation of the stent. Accordingly, when the peri-procedural adjuvant therapy procedure, is used, the compound can be delivered to the diseased site substantially contemporaneously with the placement of the stent into the patient's body and/or immediately thereafter. The compound can be the same or different as the compound delivered by the stent, i.e., the same surfactant, low molecular weight salt or drug.

In accordance with embodiment, the composition that is delivered peri-procedurally can have an increased viscosity, preferably not less than about 5 centipoise, to prolong a residence time of the adjuvantly delivered medicine in the vicinity of the injury caused by the deployment of the stent. For example, the composition to be delivered peri-procedurally can include a solution of a biologically compatible viscosifier or a blend of viscosifiers in a solvent. To prevent the viscosifier or the blend from precipitating when the composition is exposed to bodily fluids, the solvent can be water-based. The amount of water in the composition should be sufficient so as to prevent the delivered composition from forming solid masses upon exposure to blood. One example of a suitable biologically compatible viscosifier is hyaluronic acid (HA). Hyaluronic acid is a linear polysaccharide composed of disaccharide units of N-acetylglucosamine and D-glucoronic acid, having a relatively high molecular weight. Relatively high viscosities can be obtained with a relatively dilute solution of HA. Other examples of suitable, biologically compatible viscosifiers include poly(ethylene glycol) (PEG), poly(vinyl pyrrolidone) (PVP), carboxymethylcellulose (CMC), poly(ethylene imine) (PEI), poly(ethylene oxide-co-ethylene imine) (PEO-PEI), poly(vinyl alcohol) (PVOH), polyacrylamide (PAA), sulfonated dextrane, and mixtures thereof. The solvent can be water or an aqueous buffered saline solution and, in addition, can optionally include a biologically compatible, water-miscible organic solvent. The quantity of water or an aqueous buffered saline solution in the carrier is such that the viscosifier does not precipitate when the composition is exposed to bodily fluids such as blood. Typically, up to about 10.0 mass % of the organic solvent can be present in the carrier, water or an aqueous buffered saline solution constituting the balance of the carrier. Examples of water-miscible organic solvents include ethyl alcohol, acetone, dimethylsulfoxide, dimethylacetamide, and mixtures thereof.

The adjuvant delivery can be accomplished by a number of known methods. In one embodiment, the composition can be delivered using a balloon catheter. The balloon can be made from a permeable or semi-permeable material, which permits transport of the compound across the balloon wall as a result of an appropriate driving force. This driving force may be provided by several different means. For example, an electrical potential may be applied to the permeable or semi-permeable membrane to drive ionic drugs or non-ionic drugs carried in an ionic solution across the membrane in a process known as iontophoresis. Alternatively, high frequency or ultra high frequency (ultrasonic) sound waves supplied by a transducer may be used to transport drugs across the semi-permeable membrane in a process known as phonophoresis or (synonymously) sonophoresis. The compound can also be delivered simply by the application of the appropriate pressure. However, the pressure should not be too high so as to cause the compound from jetting out from the balloon and causing trauma to the vascular walls.

A modified catheter balloon which includes a balloon having a pair of spaced inflatable lobes can be also used in the adjuvant delivery procedure. After the balloon is properly positioned, the balloon lobes are inflated by introducing an inflation medium (e.g., saline solution). Inflation of the balloon lobes causes the lobes to expand so that their outer peripheral portions engage the inner surfaces of the vessel walls. This engagement defines an open space, a medicine treatment zone, between the lobes. A desired medicine is then delivered to the open space, such that the medicine is in direct contact with the vessel wall. In addition, a catheter having a double walled balloon can be also used in the adjuvant delivery procedure. Such double balloon includes an inner balloon and an outer balloon. The inner balloon is constructed of an impermeable material such as polyethylene. The outer balloon has a permeable or semi-permeable membrane and is generally concentric to the inner balloon extending completely around the inner balloon. The outer balloon is first filled with the medicine. The inner balloon is then inflated with a standard inflation medium (e.g., saline solution). As a result of inflation of the inner balloon, sufficient pressure is developed against the wall of the outer balloon (in contact with the vessel wall) to drive the medicine in the outer balloon through the wall of the outer balloon and toward the diseased site. The balloon can be the same balloon used to deliver the stent.

Suitable polymers that can be used to form the any of the coating layers for the stent include poly(ethylene-co-vinyl alcohol) (EVAL), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The polymer can be applied to the stent by dissolving the polymer in a solvent and applying the resulting composition on the stent or immersing the stent in the composition. Representative examples of some suitable solvents include N,N-dimethylacetamide (DMAC) having the formula $CH_3$—CO—$N(CH_3)_2$, N,N-dimethylformamide (DMFA) having the formula H—CO—$N(CH_3)_2$, tethrahydrofurane (THF) having the formula $C_4H_8O$, dimethylsulphoxide (DMSO) having the formula $(CH_3)_2S{=}O$, or trifluoro acetic anhydride (TFAA) having the formula $(CF_3$—$CO)_2O$.

The surfactants can be polymeric, oligomeric or low-molecular weight surfactants. Examples of suitable surfactants include poly(ethylene glycol) (PEG), PLURONIC polyols, sodium dodecyl sulfate (SDS), palmitates, stearates, tridodecylmethylammonium chloride, TWEEN surfactant as well as biologically active surfactants such as heparin stearate, heparin palmitate, surfactant protein from alveolar fluid, surfactant proteins A and D, and lung surfactant S-TA.

PEG has the formula $H[O-CH_2-CH_2-O-CH_2-CH_2-O]_nH$. PEG, a biologically compatible product, can be in an oligomeric or polymeric form and can have a molecular weight within a range of between about 500 and about 30,000 Daltons, for example, 10,000 Daltons.

PLURONIC polyols are also a biologically compatible oligomeric or polymeric substances which are various brands of poly(ethylene oxide-co-propylene oxide) having the general formula $HO[-CH_2-CH_2O-]_x[CH_2-CH_2-CH_2O-]_y[-CH_2-CH_2O-]_xH$. PLURONIC polyols are manufactured by BASF Corp. of Parsippany, N.J., and can have a molecular weight within a range of between about 950 and about 4,000 Daltons, typically, between about 1,750 and about 3,500 Daltons. "x" and "y" in the formula of PLURONIC shown above are integers selected in such a way that the terminal hydrophilic fragments (the "x" units) comprise at least about 50 weight % of the compound.

TWEEN is a trade name of a family of polyoxyethylenesorbitan monooleates and is manufactured by ICI Americas, Inc. of Bridgewater, N.J.

PEG, PLURONIC and TWEEN are examples of compounds that can serve as viscosifiers prolonging a residence time of the adjuvantly delivered medicine in the vicinity of the injury site as discussed above.

Surfactant protein from alveolar fluid, surfactant proteins A and D, and lung surfactant S-TA are all naturally occurring products which can be extracted from mammals.

Both the surfactant protein A (known as SP-A) and the surfactant protein D (known as SP-D) are hydrophilic proteins and members of a family of collagenous carbohydrate-binding proteins called collecting. All collectins have four distinct areas: an N-terminal cysteine-rich region that forms inter-chain disulfide bonds; a collagen-like region; a helical coiled-coil region; and finally a C-type lectin pattern-recognizing region known as the carbohydrate recognition domain.

SP-A is a glycoprotein with a molecular weight of about 30,000 Daltons. The human SP-A peptide comprises a sequence of 248 amino acids. Within the alveolus, SP-A exists as an octadecamer (which can be represented as eighteen units organized in a hexamer of trimers).

SP-D is the largest surfactant protein, a glycoprotein with a molecular weight of about 43,000 Daltons. The human SP-D peptide comprises a sequence of over 200 amino acids. SP-D is a dodecamer (which can be represented as twelve units organized in a tetramer of trimers).

Lung surfactant TA, known as S-TA, and also known as beractant, is often extracted from lungs of a cow. This surfactant comprises phoshpolipids modified by palmitic acid and derivatives of palmitic acid.

The drug can be any active agent for modifying the activity of vascular smooth muscle cells. It can be directed at inhibiting abnormal or inappropriate migration and/or proliferation of smooth muscle cells to inhibit restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of drugs include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

Those having ordinary skill in the art will choose an appropriate drug or a combination of drugs to be delivered via the stent and adjuvant delivery. For instance, an anti-proliferative drug can be delivered via the stent, and an anti-inflammatory drug can be delivered peri-procedurally, thus making the stent delivery complementary to the adjuvant therapy. Alternatively, an anti-inflammatory drug or anti-proliferative drug can be delivered via the stent, and an anti-coagulant drug can be delivered via adjuvant peri-procedural delivery. As another alternative, an anti-coagulant drug can be delivered via the stent, and an anti-inflammatory drug or anti-proliferative drug can be delivered via adjuvant peri-procedural delivery.

Salts can be low molecular weight salts. Examples of suitable salts include halides of alkali metals, such as sodium chloride NaCl, or potassium chloride KCl.

According to another embodiment of the present invention, other therapeutic substances that can be delivered include garlic oil, castor oil, diluted aqueous solutions of hyaluronic acid or carboxymethyl cellulose, or superoxide mimetics (SODm). Hyaluronic acid and carboxymethyl cellulose are also examples of compounds that can serve as viscosifiers prolonging a residence time of the adjuvant in the vicinity of the injury site as discussed above. In addition, certain solvents, for instance ethanol or xylene can be used as therapeutic agents in order to extract soluble lipids from the plaque.

SOD-mimetics are oxidoreductases-based complexes that contain cations of copper, iron, or manganese. SOD-mimetics are major intracellular enzymes that protects the cell against oxygen toxicity by dismutating the radical oxygen superoxide, $O_2^-$, to oxygen and hydrogen peroxide.

Manganese-based SODm, manganese(II)dichloro-aminoethylthiolated pentaazatetracyclohexacosatriene (SOD-40470) manufactured by Metaphore Pharmaceuticals, Inc. of St. Louis, Mo. is one example of SODm that can be used in the present invention as a therapeutic agent.

Embodiments of the present invention are illustrated by the following Examples.

EXAMPLE 1

A composition can be prepared by mixing the following components:
  (a) between about 0.1 mass % and about 15 mass %, for example, about 1.2 mass % of EVAL;
  (b) between about 0.05 mass % and about 1.0 mass %, for example, about 0.5 mass % of PEG; and
  (c) the balance, DMAC solvent.

The composition can be applied onto the stent and dried. The composition is applied onto the stent by any conventional method known to those having ordinary skill in the art, for example, by spraying or dipping. A primer (e.g., the above formulation without the therapeutically active compound) can be optionally applied on the surface of the bare stent. For a stent having a length of 13 mm and diameter of 3 mm, the total amount of solids of the matrix layer can be about 300 micrograms (corresponding to the thickness of between about 15 and 20 microns). "Solids" means the amount of the dry residue deposited on the stent after all volatile organic compounds (e.g., the solvent) have been removed. A composition comprising between about 0.1 mass % and about 15 mass %, for example, about 2.0 mass % of EVAL and the balance of DMAC can be applied onto the dried matrix layer to form a topcoat layer. The topcoat layer can have, for example, a total solids weight of about 200 µg.

A solution for adjuvant delivery, comprising about 0.5 mass % of hyaluronic acid (HA) and about 5 mass % of SOD-mimetic, SOD-40470, in phosphorous buffer saline solution can be prepared.

The coated stent described above can be deployed in an appropriate location in the patient's vasculature using any suitable surgical method known to those having ordinary skill in the art. During the process of implantation of the coated stent and immediately thereafter, the solution for adjuvant delivery can be administered peri-procedurally. The method of administration as well as the duration of the peri-procedural adjuvant therapy can be selected by those having ordinary skill in the art.

EXAMPLE 2

A composition can be prepared by mixing the following components:
  (a) between about 0.1 mass % and about 15 mass %, for example, about 2.0 mass % of EVAL;
  (b) between about 0.05 mass % and about 1.0 mass %, for example, about 0.7 mass % of EVEROLIMUS; and
  (c) the balance, DMAC solvent.

The composition can be applied onto a stent to form a matrix layer with about 200 µg of total solids. A composition comprising between about 0.1 mass % and about 15 mass %, for example, about 2.0 mass % of EVAL and the balance of DMAC can be applied onto the dried matrix layer to form a topcoat layer. The topcoat layer can have, for example, a total solids weight of about 300 µg. Following the formation of the topcoat layer, a composition comprising between about 0.1 mass % and about 10 mass %, for example, about 1.3 mass % of EVAL, between about 0.1 mass % and about 1.5 mass %, for example, about 0.7 mass % of PEG and the balance of DMAC, can be applied onto the dried topcoat layer to form a finishing coat. The finishing coat can have, for example, a total solids weight of about 200 µg.

A solution for adjuvant delivery, comprising about 5 mass % of SOD-40470, about $10^{-8}$ moles (M) of paclitaxel (PT) and about 2 mass % of carboxymethyl cellulose (CMC) in phosphorous buffer saline solution can be prepared.

The coated stent described above can be deployed in a patient via a porous balloon and the solution for adjuvant delivery concomitantly.

EXAMPLE 3

A composition can be prepared by mixing the following components:
  (a) between about 0.1 mass % and about 15 mass %, for example, about 2.0 mass % of EVAL;
  (b) between about 0.05 mass % and about 1.0 mass %, for example, about 0.7 mass % of EVEROLIMUS; and
  (c) the balance, DMAC solvent.

The composition can be applied onto a stent to form a matrix layer with about 200 µg of total solids. A composition comprising between about 0.1 mass % and about 15 mass %, for example, about 2.0 mass % of EVAL and the balance of DMAC can be applied onto the dried matrix layer to form a topcoat layer. The topcoat layer can have, for example, a total solids weight of about 300 µg. Following the formation of the topcoat layer, a composition comprising between about 0.1 mass % and about 10 mass %, for example, about 1.0 mass % of EVAL, between about 0.1 mass % and about 1.5 mass %, for example, about 1.0 mass % of heparin-tridodecylmethylammonium chloride (TDMAC), and the balance of a 4:1 by mass blend of solvents DMAC and DMSO, can be applied onto the dried topcoat layer to form a finishing coat. The finishing coat can have, for example, a total solids weight of about 200 µg.

A solution for adjuvant delivery, comprising about 5 mass % of SOD-40470 and about 2 mass % of heparin in phosphorous buffer saline solution can be prepared.

The coated stent described above can be deployed and the solution delivered concomitantly.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for inhibiting restenosis comprising:
  (a) implanting a stent at a treatment site in a patient's vasculature, wherein the stent comprises a drug-polymer layer including a first drug, therapeutic agent, medicine, compound or active agent; and
  (b) peri-procedurally delivering a solution comprising a second drug, therapeutic agent, medicine, compound or active agent to the treatment site intraluminally, wherein the peri-procedural deliverance of the second drug, therapeutic agent medicine, compound or active agent occurs substantially contemporaneously with, and/or immediately after, the implantation of the stent, further, wherein the solution has a viscosity of not less than 5 centipoise to prolong the residence time of the solution at the treatment site, wherein the solution further comprises a viscosifier for increasing the viscosity of the solution, and still further, wherein the solution includes (a) up to about 10 mass % of a biologically compatible water-miscible organic solvent and (b) an amount of water or aqueous buffered saline solution to prevent the second drug, therapeutic agent, medicine, compound or active agent and the viscosifier from precipitating when the composition is exposed to blood.

2. The method of claim 1, wherein the first or second drug, therapeutic agent, medicine, compound or active agent comprises a surfactant that is selected from a group consisting of poly(ethylene glycol), a poly(ethylene oxide-co-propylene oxide), palmitates, stearates, tridodecylmethylammonium chloride, a polyoxyethylenesorbitan monooleate, sodium dodecyl sulfate, heparin stearate, heparin palmitate, surfactant protein from alveolar fluid, surfactant protein A, surfactant protein D, lung surfactant S-TA, and combinations thereof.

3. The method of claim 2, wherein the poly(ethylene oxide-co-propylene oxide) is represented by a formula:

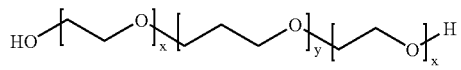

wherein x is an integer representing a number of ethylene oxide fragments, y is an integer representing a number of propylene oxide fragments, and the integers are selected such that the molecular weight of the polyol ranges from about 950 to about 4000 Daltons.

4. The method of claim 3, wherein x is selected such that the terminal ethylene oxide fragments comprise at least about 50% (w/w) of the compound.

5. The method of claim 1, wherein the first or second drug, therapeutic agent, medicine, compound or active agent is selected from a group consisting of estradiol, paclitaxel, hirudin, recombinant hirudin, heparin, heparinoids, sodium heparin, heparin derivatives containing hydrophobic counterions, docetaxel, everolimus, rapamycin, structural derivatives of rapamycin, functional analogs of rapamycin, and nitric oxide.

6. The method of claim 5, wherein the heparin derivative is heparin-tridodecylmethylammonium chloride.

7. The method of claim 1, wherein the first or second drug, therapeutic agent, medicine, compound or active agent is selected from the group consisting of sodium chloride, potassium chloride, or a combination thereof.

8. The method of claim 1, wherein the first or second drug, therapeutic agent, medicine, compound or active agent is selected from a group consisting of garlic oil, castor oil, hyaluronic acid, carboxymethyl cellulose, ethanol, xylene, and superoxide mimetics, and combinations thereof.

9. The method of claim 1, wherein the first or second drug, therapeutic agent, medicine, compound or active agent comprises a low molecular weight salt of a size that can penetrate cells of tissue at a diseased site.

10. The method of claim 1, wherein the first or second drug, therapeutic agent, medicine, compound or active agent is selected from the group consisting of an antiproliferative, antineoplastic, antiinflammatory, antiplatelet, antianticoagulant, antifibrin, antithrombin, antimitotic, antibiotic, antiallergic, antioxidant, or a combination thereof.

11. The method of claim 1, wherein the first or second drug, therapeutic agent, medicine, compound or active agent comprises an alkali metal halide.

12. The method of claim 1, wherein the viscosifier is selected from a group consisting of poly(ethylene glycol), poly(vinyl pyrrolidone), carboxymethylcellulose, poly(ethylene imine), poly(ethylene oxide-co-ethylene imine), poly(vinyl alcohol), polyacrylamide, sulfonated dextrane, and combinations thereof.

13. A method for inhibiting restenosis comprising:
(a) implanting a stent at a treatment site in a patient's vasculature, wherein the stent comprises a first drug, therapeutic agent, medicine, compound or active agent and a surfactant; and
(b) peri-procedurally delivering a solution comprising a second drug, therapeutic agent, medicine, compound or active agent to the treatment site intraluminally, wherein the per-procedural deliverance occurs substantially contemporaneously with, and/or immediately after, implantation of the stent in the patient's vasculature, wherein none of the components within the solution forms a solid mass upon exposure to blood, and wherein the solution further comprises a viscosifier for increasing the viscosity of the solution, wherein the solution further includes (a) up to about 10 mass % of a biologically compatible water-miscible organic solvent and (b) an amount of water or aqueous buffered saline solution to prevent the second drug, therapeutic agent, medicine, compound or active agent and the viscosifier from precipitating when the composition is exposed to blood.

14. The method of claim 13, wherein the solution has a viscosity of not less than 5 centipoise.

15. The method of claim 13, wherein the drug, therapeutic agent, medicine, compound or active agent is selected from the group consisting of an antiproliferative, antineoplastic, antiinflammatory, antiplatelet, antianticoagulant, antifibrin, antithrombin, antimitotic, antibiotic, antiallergic, antioxidant, or a combination thereof.

16. The method of claim 13, wherein the drug, therapeutic agent, medicine, compound or active agent is selected from a group consisting of poly(ethylene glycol), a poly(ethylene oxide-co-propylene oxide), palmitates, stearates, tridodecylmethylammonium chloride, a polyoxyethylenesorbitan monooleate, sodium dodecyl sulfate, heparin stearate, heparin palmitate, surfactant protein from alveolar fluid, surfactant protein A, surfactant protein D, lung surfactant S-TA, and combinations thereof.

17. The method of claim 16, wherein the poly(ethylene oxide-co-propylene oxide) is represented by a formula:

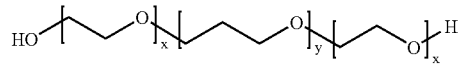

wherein x is an integer representing a number of ethylene oxide fragments, y is an integer representing a number of propylene oxide fragments, and the integers are selected such that the molecular weight of the polyol ranges from about 950 to about 4000 Daltons.

18. The method of claim 17, wherein x is selected such that the terminal ethylene oxide fragments comprise at least about 50% (w/w) of the compound.

19. The method of claim 13, wherein the drug, therapeutic agent, medicine, compound or active agent is selected from a group consisting of estradiol, paclitaxel, hirudin, recombinant hirudin, heparin, heparinoids, sodium heparin, heparin derivatives containing hydrophobic counter-ions, docetaxel, everolimus, rapamycin, structural derivatives of rapamycin, functional analogs of rapamycin, and nitric oxide.

20. The method of claim 19, wherein the heparin derivative is heparin-tridodecylmethylammonium chloride.

21. The method of claim 13, wherein the drug, therapeutic agent, medicine, compound or active agent is selected from a group consisting of garlic oil, castor oil, hyaluronic acid, carboxymethyl cellulose, ethanol, xylene, and superoxide mimetics, and combinations thereof.

22. The method of claim 13, wherein the drug, therapeutic agent, medicine, compound or active agent comprises a low molecular weight salt of a size that can penetrate cells of tissue at a diseased site.

23. The method of claim 13, wherein the drug, therapeutic agent, medicine, compound or active agent comprises an alkali metal halide.

24. The method of claim 13, wherein the drug, therapeutic agent, medicine, compound or active agent is selected from the group consisting of sodium chloride, potassium chloride, or a combination thereof.

25. The method of claim 13, wherein the viscosifier is selected from a group consisting of poly(ethylene glycol), poly(vinyl pyrrolidone), carboxymethylcellulose, poly(ethylene imine), poly(ethylene oxide-co-ethylene imine), poly(vinyl alcohol), polyacrylamide, sulfonated dextrane, and combinations thereof.

26. The method of claim 13, wherein the surfactant is selected from a group consisting of poly(ethylene glycol), a poly(ethylene oxide-co-propylene oxide), palmitates, stearates, tridodecylmethylammonium chloride, a polyoxyethylenesorbitan monooleate, sodium dodecyl sulfate, heparin stearate, heparin palmitate, surfactant protein from alveolar fluid, surfactant protein A, surfactant protein D, lung surfactant S-TA, and combinations thereof.

27. A method for inhibiting restenosis comprising:
(a) implanting a stent at a treatment site in a patient's vasculature, wherein the stent comprises a first drug, therapeutic agent, medicine, compound or active agent; and
(b) peri-procedurally delivering a solution comprising a second drug, therapeutic agent, medicine, compound or active agent to the treatment site intraluminally, wherein the peri-procedural deliverance occurs substantially contemporaneously with, and/or immediately after, the implantation of the stent in the patient's vasculature, wherein the solution has a viscosity of not less than 5 centipoise to prolong the residence time of the solution at the treatment site, wherein none of the components within the solution forms a solid mass upon exposure to blood, and wherein the solution further comprises a viscosifier for increasing the viscosity of the solution,
wherein the solution further includes (a) up to about 10 mass % of a biologically compatible water-miscible organic solvent and (b) an amount of water or aqueous buffered saline solution to prevent the second drug, therapeutic agent, medicine, compound or active agent and the viscosifier from precipitating when the composition is exposed to blood.

28. The method of claim 27, wherein the drug, therapeutic agent, medicine, compound or active agent is selected from the group consisting of an antiproliferative, antineoplastic, antiinflammatory, antiplatelet, antianticoagulant, antifibrin, antithrombin, antimitotic, antibiotic, antiallergic, antioxidant, or a combination thereof.

29. The method of claim 27, wherein the drug, therapeutic agent, medicine, compound or active agent is selected from a group consisting of poly(ethylene glycol), a poly(ethylene oxide-co-propylene oxide), palmitates, stearates, tridodecylmethylammonium chloride, a polyoxyethylenesorbitan monooleate, sodium dodecyl sulfate, heparin stearate, heparin palmitate, surfactant protein from alveolar fluid, surfactant protein A, surfactant protein D, and lung surfactant S-TA, and combinations thereof.

30. The method of claim 29, wherein the poly(ethylene oxide-co-propylene oxide) is represented by a formula:

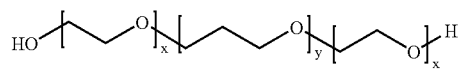

wherein x is an integer representing a number of ethylene oxide fragments, y is an integer representing a number of propylene oxide fragments, and the integers are selected such that the molecular weight of the polyol ranges from about 950 to about 4000 Daltons.

31. The method of claim 30, wherein x is selected such that the terminal ethylene oxide fragments comprise at least about 50% (w/w) of the compound.

32. The method of claim 27, wherein the drug, therapeutic agent, medicine, compound or active agent is selected from a group consisting of estradiol, paclitaxel, hirudin, recombinant hirudin, heparin, heparinoids, sodium heparin, heparin derivatives containing hydrophobic counter-ions, docetaxel, everolimus, rapamycin, structural derivatives of rapamycin, functional analogs of rapamycin, and nitric oxide.

33. The method of claim 32, wherein the heparin derivative is heparin-tridodecylmethylammonium chloride.

34. The method of claim 27, wherein the drug, therapeutic agent, medicine, compound or active agent is selected from a group consisting of garlic oil, castor oil, hyaluronic acid, carboxymethyl cellulose, ethanol, xylene, superoxide mimetics, and combinations thereof.

35. The method of claim 27, wherein the drug, therapeutic agent, medicine, compound or active agent comprises a low molecular weight salt of a size that can penetrate cells of tissue at a diseased site.

36. The method of claim 27, wherein the drug, therapeutic agent, medicine, compound or active agent comprises an alkali metal halide.

37. The method of claim 27, wherein the drug, therapeutic agent, medicine, compound or active agent is selected from the group consisting of sodium chloride, potassium chloride, or a combination thereof.

38. The method of claim 27, wherein the viscosifier is selected from a group consisting of poly(ethylene glycol), poly(vinyl pyrrolidone), carboxymethylcellulose, poly(ethylene imine), poly(ethylene oxide-co-ethylene imine), poly(vinyl alcohol), polyacrylamide, sulfonated dextrane, and combinations thereof.

* * * * *